United States Patent [19]

Shi et al.

[11] Patent Number: 5,683,823

[45] Date of Patent: Nov. 4, 1997

[54] WHITE LIGHT-EMITTING ORGANIC ELECTROLUMINESCENT DEVICES

[75] Inventors: Jianmin Shi, Webster; Ching Wan Tang, Rochester, both of N.Y.

[73] Assignee: Eastman Kodak Company, Rochester, N.Y.

[21] Appl. No.: 592,830

[22] Filed: Jan. 26, 1996

[51] Int. Cl.$^6$ .................................... H05B 33/14
[52] U.S. Cl. ..................... 428/690; 428/691; 428/917; 313/503; 313/504
[58] Field of Search .................. 428/690, 691, 428/917; 313/504, 503

[56] References Cited

U.S. PATENT DOCUMENTS

| | | | |
|---|---|---|---|
| 5,150,006 | 9/1992 | VanSlyke et al. | 313/504 |
| 5,326,692 | 7/1994 | Brinkley et al. | 435/6 |
| 5,405,709 | 4/1995 | Littman et al. | 428/690 |
| B1 5,326,692 | 4/1996 | Brinkley et al. | 435/6 |

*Primary Examiner*—Charles Nold
*Attorney, Agent, or Firm*—Raymond L. Owens

[57] ABSTRACT

An electroluminescent device includes an anode, a positive-hole transporting layer made of an organic compound, a fluorescent emitting layer made of an organic compound, a cathode. The fluorescent emitting layer includes a red light emitting material uniformly dispersed in a host emitting material. The host emitting material being adapted to emit in the blue green regions so that the light produced by this device is substantially white.

5 Claims, 1 Drawing Sheet

WHITE LIGHT-EMITTING ORGANIC ELECTROLUMINESCENT DEVICES

FIELD OF THE INVENTION

This invention relays to organic electroluminescent (EL) devices. More specifically, the invention relates to organic electroluminescent devices which emit white light from a current conducing organic layer.

BACKGROUND OF THE INVENTION

The organic electroluminescent devices which emit white light from a current conducing organic layer have very important applications. The applications of such a device include paper-thin light sources, a backlight for liquid crystal display, and full color displays achieved by combing the emitters with micropatterned color filters. The following patents and publications disclose the preparation of organic EL devices, capable of emitting white light, comprising a hole transporting layer and an organic luminescent layer, and interposed between a pair of electrodes.

Sato in JP 07,142,169 discloses an organic electroluminescent device, capable of emitting white light, is made by staking a blue light emitting layer next to the hole transporting layer and followed by a green light emitting layer having a region containing a red fluorescent dye.

Kido et al., in Science, Vol. 267, p. 1332, (1995), also in Appl. Phys. Lett. Vol. 64, p. 815, (1994), report a white light-emitting organic electroluminescent device. In this device, three emitter layers with different carrier transport properties, each emitting blue, green, or red light, are used to generate white light.

Litman et al. in U.S. Pat. No. 5,405,709 discloses another emitting organic electroluminescent device which is capable of emitting white light in response to hole-electron recombination and comprises a fluorescent material and a mixed ligand aluminum chelate.

Tokailin et al. in U.S. Pat. No. 5,126,214 taught an electroluminescent element comprising a electroluminescent layer which emits a blue light and a fluorescent layer spaced from the electroluminescent layer. The fluorescent layer absorbs the blue light generated by the electroluminescent layer and fluorescent in a visible light range from bluish green to red. The disclosed element is capable of producing white light.

However, these EL devices require the use of multiple layers of organic luminescent materials. In order to produce white light, each luminescent layer is necessarily doped with one or more fluorescent dyes. Thus, the fabrication process is complicated. Furthermore, the emission color may vary, depending on the drive conditions because small changes in voltage may cause electron-hole recombination to take place in different layers producing color variations.

The related improvement in organic EL devices have been disclosed in U.S. Pat. Nos: 5,151,629; 5,150,006; 5,141,671; 5,073,446; 5,061,569; 5,059,862; 5,059,861; 5,047,687; 4,950,950; 4,769,292, 5,104,740; 5,227,252; 5,256,945; 5,069,975, and 5,122,711.

SUMMARY OF THE INVENTION

It is an object of this invention is to provide a simple electroluminescent device which is capable of emitting white light efficiently.

This object is achieved in an electroluminescent device, comprising:

a) an anode;

b) a hole transporting layer made of an organic compound;

c) a luminescent layer including a host material and a guest component;

d) a cathode; and e) the guest component of the luminescent layer includes a red light emitting material uniformly dispersed in the host material, said host material being adapted to emit blue green light so that the light produced is substantially white.

Upon electric excitation by either a DC or AC voltage source, luminescence is produced from this host-guest luminescent layer. Depending on the concentration of the guest molecule in the host, the color of the electroluminescence varies from the blue-green fluorescence of the pure host solid to the red fluorescence of the guest molecule. By selecting an appropriate guest concentration in the host, combination of these two emissions is produced, resulting in white electroluminescence.

ADVANTAGES

An advantage of the present invention is that the EL device structure is simple, using a single luminescent layer to produce white light. In particular, the materials of this invention when used as guest dopants in a host material provide a unique combination for producing a white EL device. It is also a feature that a single guest component in the host material can be effectively employed.

Another advantage is that this white EL device is efficient and stable and should be useful in display and lighting applications.

DETAILED DESCRIPTION OF THE PREFERRED EMBODIMENTS

Figure 1:
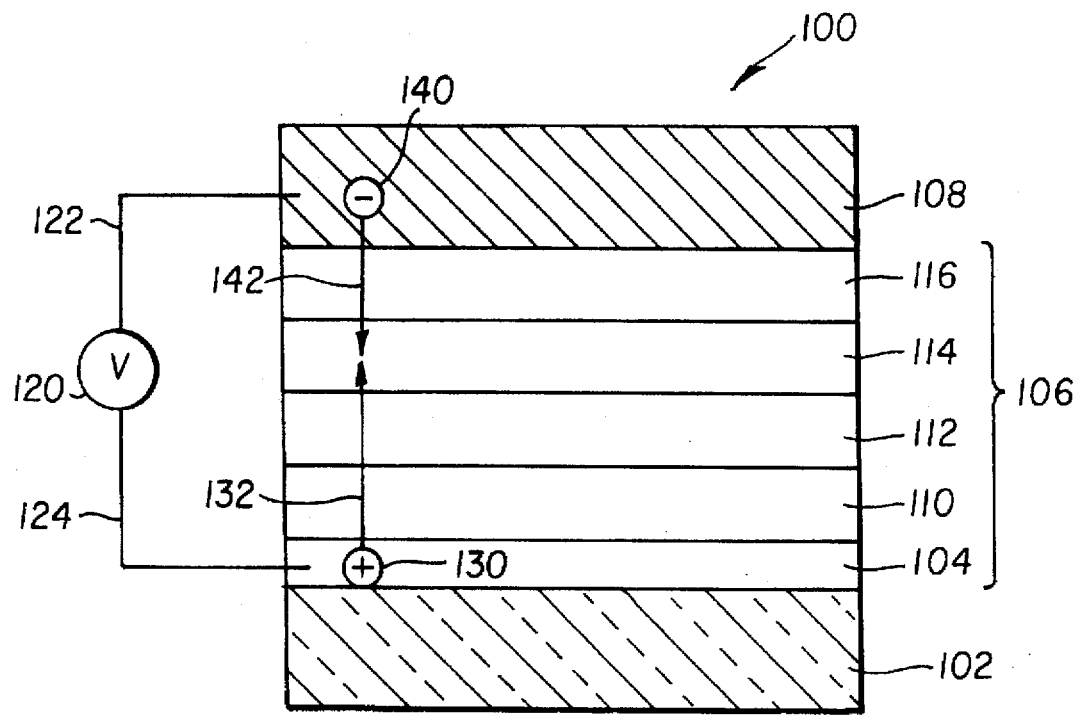
FIG. 1 is a schematic cross-sectional view of an electroluminescent device in accordance with the invention. For convenience of illustration, it will be understood that various layers are not to scale since other than the glass layer, they are in the submicron range.

Referring now to FIG. 1, an electroluminescent (EL) device 100 is shown. The device is formed on a glass substrate 102. This glass substrate can be borosilicate or soda lime. On the glass substrate 102 there is provided a layer 104 which forms the anode of the device 100. The anode layer typically can be formed from indium tin oxide. On the anode, in sequence, there are provided the following layers, hole injection layer 110, hole transport layer 112, luminescent layer 114 and electron transport layer 116. The layers 110, 112, 114 and 116 all comprise the organic electroluminescent medium 106. On the medium 106 or the electron transport layer 116, is formed the cathode 108. The anode and cathode are connected to an external AC or DC power source 120 conductors 122 and 124, respectively. The power source can be pulsed or continuous wave (CW).

The device 100 can be viewed as a diode which is forward biased. Under these conditions injection of hole 130 (positive charge carrier) from anode 104 occurs into the lower organic layer, as schematically shown in FIG. 1, while electron (negative charge carrier) are injected into the upper organic layer, as schematically shown at 140, into the luminescent medium. The injected holes and electrons each migrate toward the oppositely charged electrode, as shown by the arrows 132 and 142, respectively. This results in hole-electron recombination. When a migrating electron drops from its conduction band to a valence band in filling a hole, energy is released as light. Hence the organic luminescent medium forms between the electrodes a luminescence zone receiving mobile charge carriers form each electrode. Depending upon the choice of alternative constructions, the released light can be emitted from the organic luminescent material through the anode, through the cathode, or through any combination of the foregoing.

Figure 2:
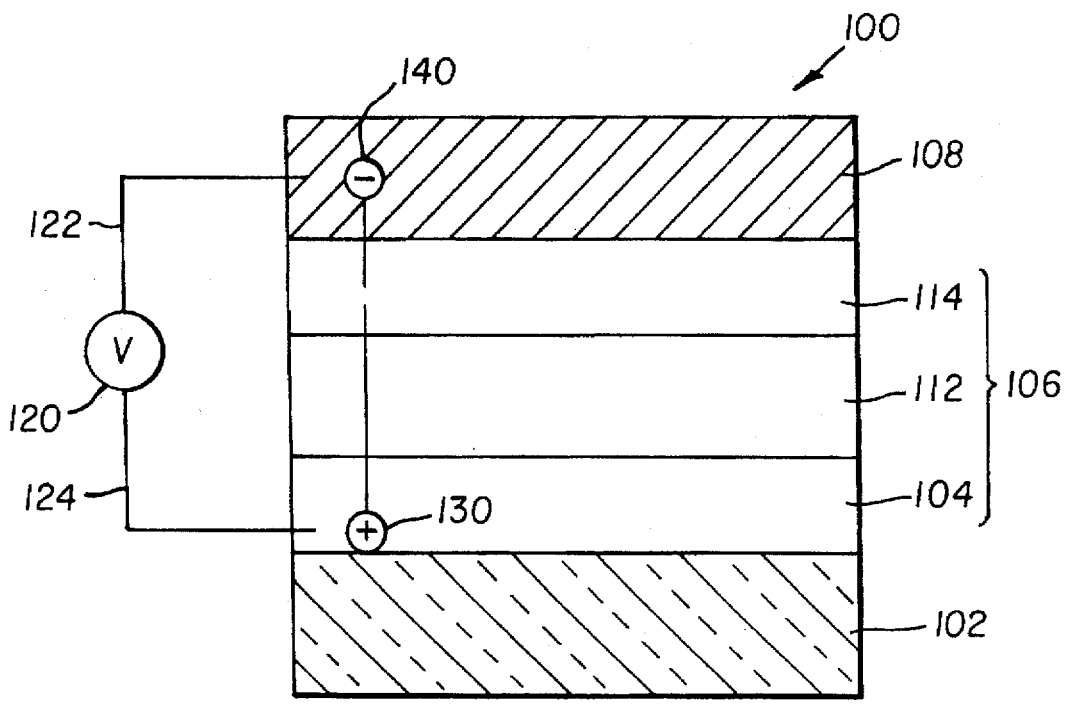
FIG. 2 is a schematic cross-sectional view of an alternative construction of an electroluminescent device in accordance with the invention. For convenience of illustration, it will be understood that various layers are not to scale since other than the glass layer, they are in the submicron range.

An alternative construction of the EL device is shown in FIG. 2. In this structure, the hole-injection layer 110 and the electron-injection layer 116 of EL device 100 are omitted. The EL performance based on this simplified structure would still be functional provided the electrode contacts can adequately inject charge carriers into the EL medium. This means that the potential barrier between the anode 104 and the hole-transport layer 112 is sufficiently low such that hole injection from the anode to the hole-transport layer is relatively unimpeded when the device is biased with a low voltage. Likewise, the potential barrier between the cathode 108 and the luminescent layer 114 is sufficiently low such that the electron injection from the cathode to the luminescent layer is also unimpeded. It is understood that in this structure the luminescent layer is capable of electron transport as well as electron-hole recombination is necessary for the production of electroluminescence.

Other alternative constructions of the EL device based on FIG. 1 are possible. For instance, one such construction would omit only the hole-injection layer 110, but retain all the other layers. Another construction would omit only the electron injection layer 116, but retain all other layers. The criteria for selecting one of these alternative construction is based on a combination of factors, such as the injection properties of the electrode contacts, the ionization potentials of the individual layers in contact with the electrodes as well as the transport characteristics of the individual organic layer comprising the EL medium.

The hole injection layer 110 of EL device 100 contains a porphyrinic compound. A porphyrinic compound is any compound, natural or synthetic, which is derived from or includes a porphyrin structure, including porphine itself. Any of the prophyrinic compounds disclosed by Adler, U.S. Pat. No. 3,935,031 or Tang U.S. Pat. No. 4,356,429, the disclosures of which are here incorporated by reference, can be employed.

Preferred porphyrinic compounds are those of structural formula (III):

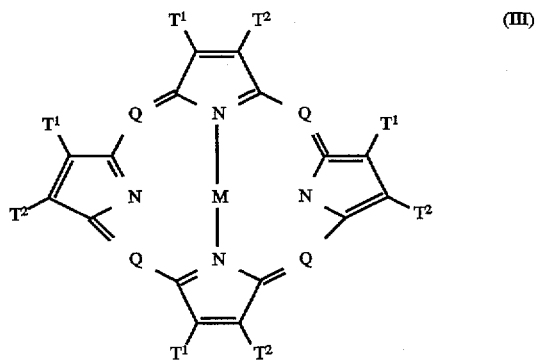

wherein

Q is N or C—R;

M is a metal, metal oxide, or metal halide;

R is hydrogen, alkyl, aralkyl, aryl, or alkaryl; and $T^1$ and $T^2$ represent hydrogen or together complete a unsaturated six member ring, which can include substituents, such as alkyl or halogen. Preferred six membered rings are those formed of carbon, sulfur, and nitrogen ring atoms. Preferred alkyl moieties contain from about 1 to 6 carbon atoms while phenyl constitutes a preferred aryl moiety.

In an alternative preferred form the porphyrinic compounds differ from those of structural formula (III) by substitution of two hydrogens for the metal atom, as indicated by formula (IV):

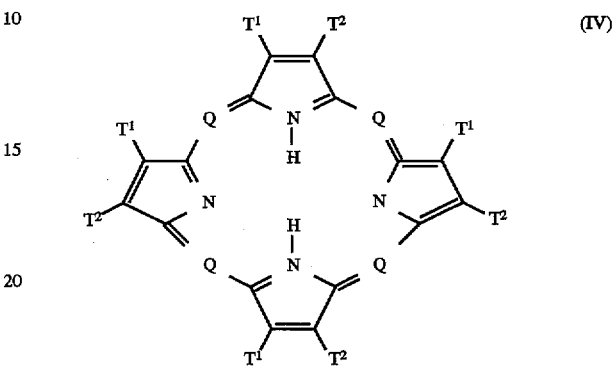

Highly preferred examples of useful porphyrinic compounds are metal free phthalocyanines and metal containing phthalocyanines. While the porphyrinic compounds in general and the phthalocyanines in particular can contain any metal, the metal preferably has a positive valence of two or higher. Exemplary preferred metals are cobalt, magnesium, zinc, palladium, nickel, and, particularly, copper, lead, and platinum.

Illustrative of useful porphyrinic compounds are the following:

Prophine 1,10,15,20-tetraphenyl-21H,23H-porphine copper (II)

1,10,15,20-tetrapheyl-21H,23H-porphine zinc (II)

Copper phthlocyanine

Chromium phthalocyanine fluoride

The hole transporting layer of the organic EL device contains at least one hole transporting aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monarylamine, diarylamine, triarylamine, or a polymeric arylamine. Exemplary monomeric triarylamines are illustrated by Klupfel et at. U.S. Pat. No. 3,180,730. Other suitable triarylamines substituted with vinyl or vinyl radicals and/or containing at least one active hydrogen containing group are disclosed by Brantley et at. U.S. Pat. Nos. 3,567,450 and 3,658,520.

Another class of aromatic tertiary amines are those which include at least two aromatic tertiary amine moieties. Such compounds include those represented by structural formula (V).

wherein $Q^1$ and $Q^2$ are independently aromatic tertiary amine moieties, and

G is a linking group such as an arylene, cycloalkylene, or alkylene group of a carbon to carbon bond.

A preferred class of triarylamines satisfying structural formula (V) and containing two triarylamine moieties are those satisfying structural formula (VI):

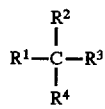

where $R^1$ and $R^2$ each independently represents a hydrogen atom, an aryl group, or an alkyl group or $R^1$ and $R^2$ together represent the atoms completing a cycloalkyl group, and $R^3$ and $R^4$ each independently represents an aryl group which is in turn substituted with a diaryl substituted amino group, as indicated by structural formula (VII):

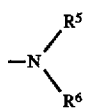

wherein $R^5$ $R^6$ are independently selected aryl groups.

Another preferred class of aromatic tertiary amines are tetraaryldiamines. Preferred tetraaryldiamines include two diarylamino groups, such as indicated by formula (VIII), linked through an arylene group:

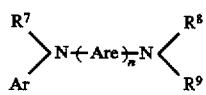

wherein

Are is an arylene group, n is an integer of from 1 to 4, and

Ar, $R^7$, $R^8$, and $R^9$ are independently selected aryl groups.

The various alkyl, alkylene, aryl, and arylene moieties of the foregoing structural formulae (V), (VI), (VIII), can each in turn be substituted. Typical substituents including alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms e.g., cyclopentyl, cyclohexyl, and cycloheptyl ring structures. The aryl and arylene moieties are preferably phenyl and phenylene moieties wherein Are is an arylene group, n is an integer of from 1 to 4, and Ar, $R^7$, $R^8$, and $R^9$ are independently selected aryl groups.

The various alkyl, alkylene, aryl, and arylene moieties of the foregoing structural formulae (V), (VI), (VIII), can each in turn be substituted. Typical substituents including alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ting carbon atoms-e.g., cyclopentyl, cyclohexyl, and cycloheptyl ring structures. The aryl and arylene moieties are preferably phenyl and phenylene moieties.

Illustrative of useful hole transport compounds are the following:

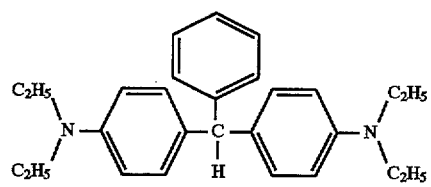

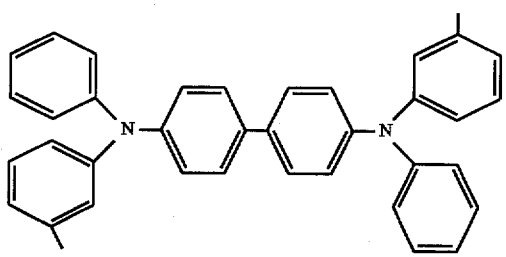

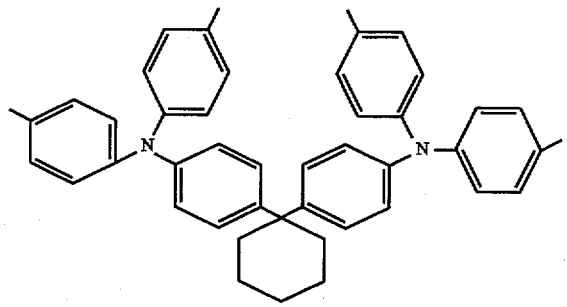

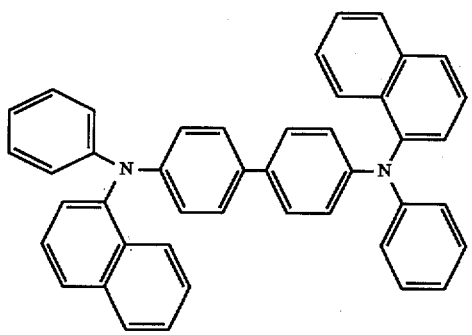

The luminescent layer emitting white light in device 100 comprises of a host organic material uniformly doped with a small amount of a guest material.

It is desired to blend with minor amounts of each of one or more fluorescent materials capable of emitting broad band red light and one or more fluorescent materials capable of emitting broad band blue light, the concentrations of each of the materials being selected to produce white emitted light.

The guest materials of luminescent layer of device 100 contains a fluorescent compound represented by structural formula I:

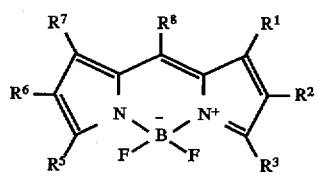

wherein $R^1$-$R^8$, which may be the same or different, are hydrogen, halogen, or alkyl, alkoxy, alkenyl, cycloalkyl, arylalkyl, acyl, wherein the alkyl portions each contain fewer than 24 carbons, or aryl heteroaryl, alone or in combination.

This class of fluorescent compounds is known in its use as fluorescent probes because of its high quantum efficiency of fluorescence and other optical properties. For reference, see U.S. Pat. No. 5,326,692 and literature cited therein. Particularly useful in organic EL application of the present invention are the following specific compounds.
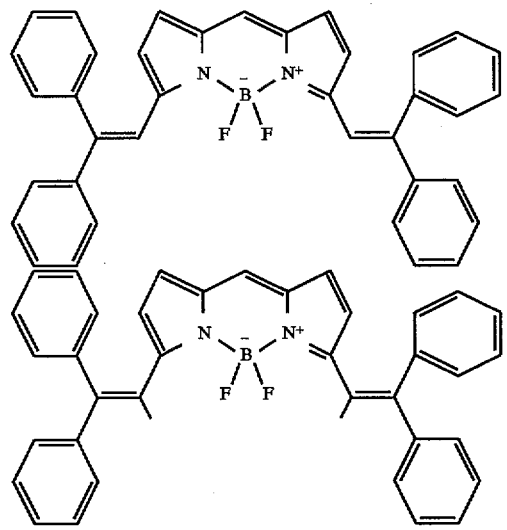
G1
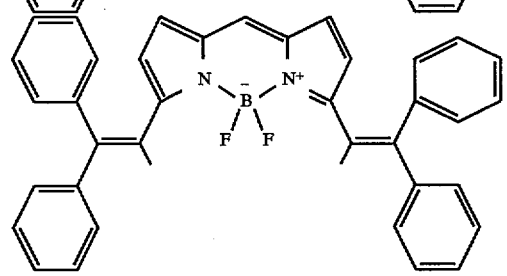
G2
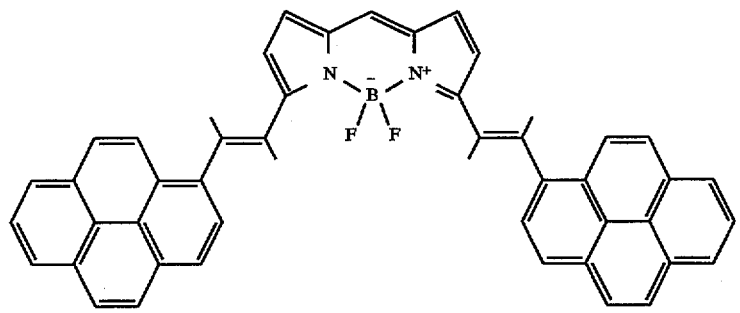
G3
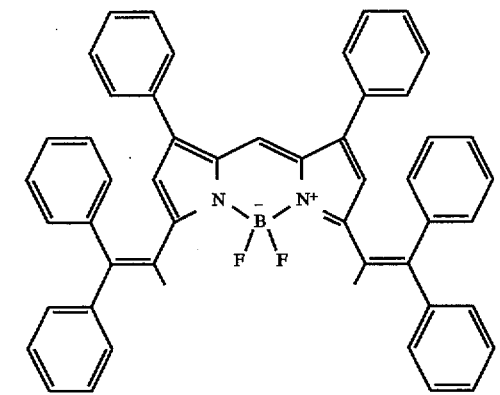
G4
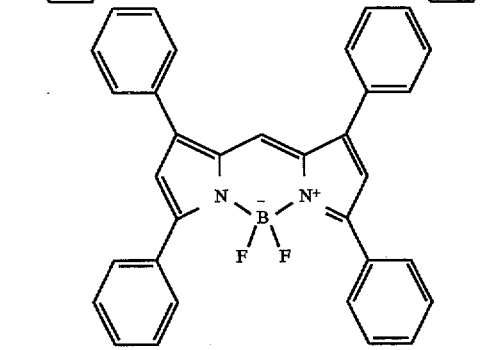
G5

-continued
G6
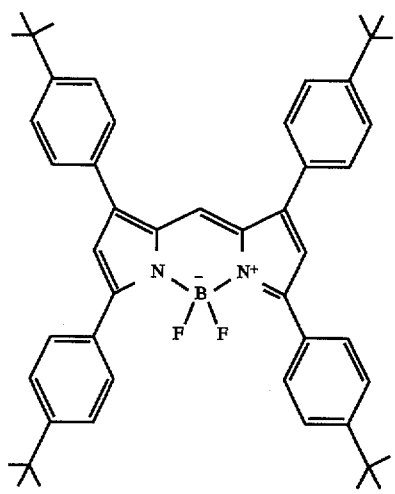
G7
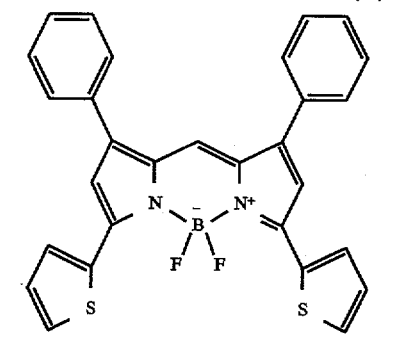
G8
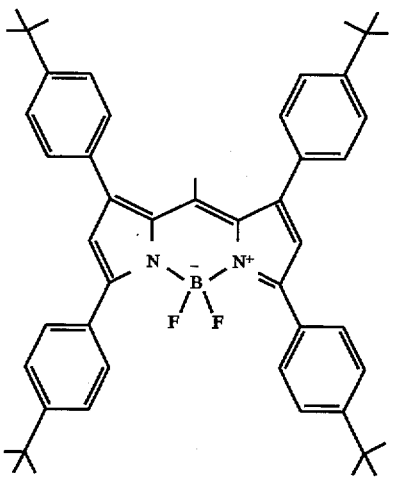
G9
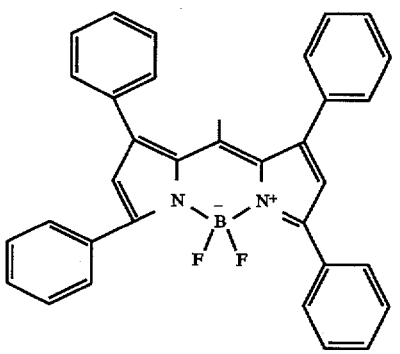

-continued

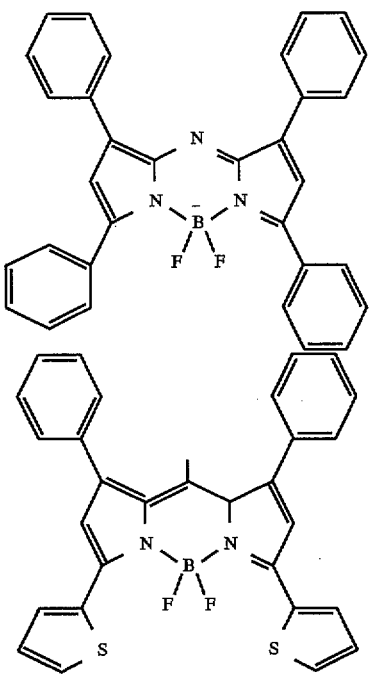
G10

G11

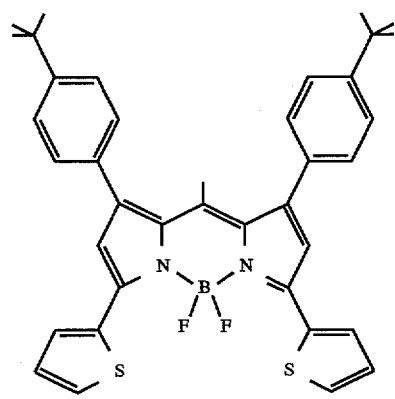

G12

The host materials of luminescent layer of device 100 contains the compounds that emit blue green electroluminescence. Preferably, the host compound is a mixed ligand aluminum chelate, specifically a bis($R^S$-8-quinolinolato)(phenolato)aluminum(III) chelate of formula II,

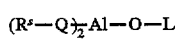  II wherein Q in each occurrence represents a substituted 8-quinolinolato ligand, $R^S$ represents an 8-quionolinolato ring substituent chosen to block sterically the attachment of more than two substituted 8-quinolinolato ligands to the aluminum atoms, O—L is a phenolato ligand, and L is a hydrocarbon group that includes an aryl moiety.

The following constitute specific examples of preferred mixed ligand aluminum chelates useful for the practice of the present invention; other suitable materials are shown in columns 12–17 of U.S. Pat. No. 5,150,006, the disclosures of which are incorporated herein by reference:

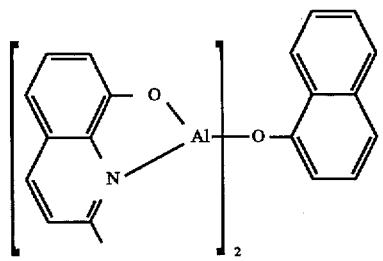
H1

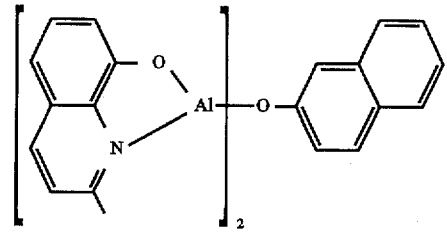
H2
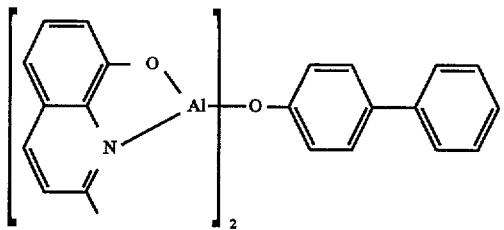
H3
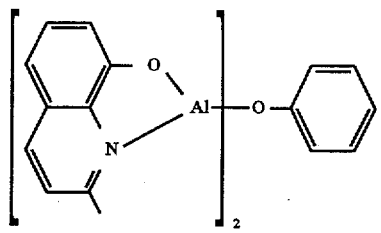
H4
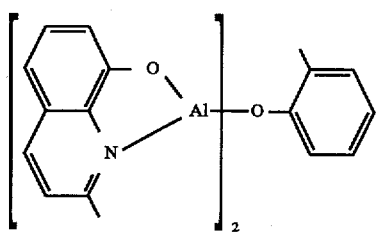
H5
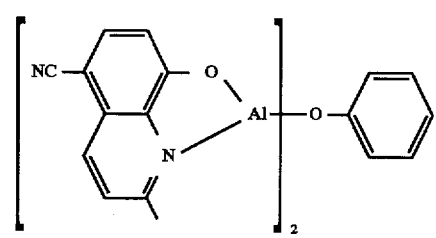
H6
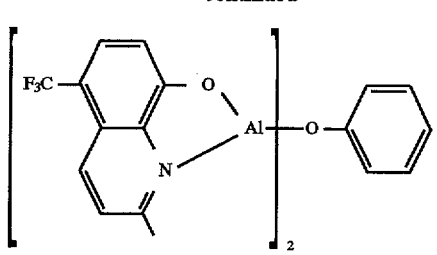
H7
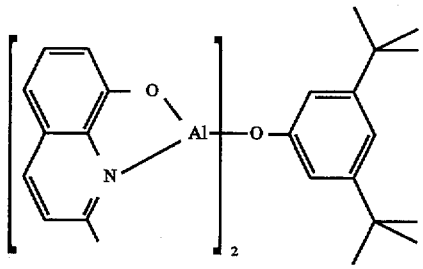
H8
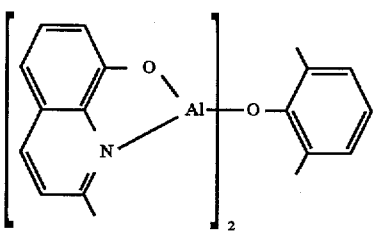
H9
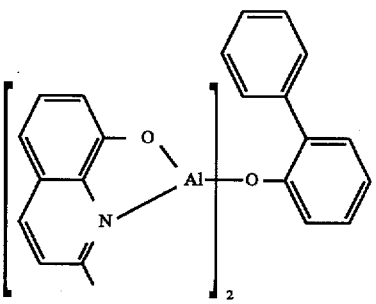
H10
Still other host materials which can be employed in this invention are optical brighteners, particularly those disclosed by VanSlyke et at. U.S. Pat. No. 4,539,507, cited above and herein incorporated by reference. Useful optical brighteners include those satisfying structural formulae (VIII), (IX) and (X):
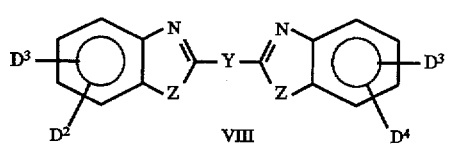
or -continued

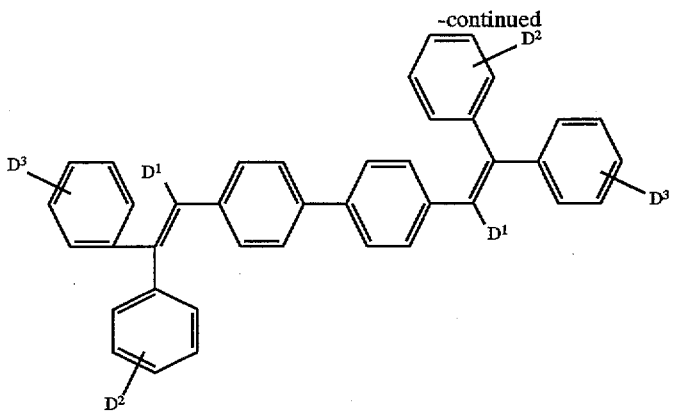

wherein:

$D^1$, $D^2$, $D^3$, and $D^4$ are individually hydrogen; saturated aliphatic of from 1 to 10 carbon atoms, for example, propyl, t-butyl, heptyl, and the like; aryl of from 6 to 10 carbon atoms, for example, phenyl and naphthyl; or halo such as chloro, fluoro, and the like; or $D^1$ and $D^2$ or $D^3$ and $D^4$ taken together comprise the atoms necessary to complete a fused aromatic ring optionally bearing at least one saturated aliphatic of from 1 to 10 carbon atoms, such as methyl, ethyl, propyl and the like;

$D^5$ is a saturated aliphatic of from 1 to 20 carbon atoms, such as methyl, ethyl, n-eicosyl, and the like; aryl of from 6 to 10 carbon atoms, for example, phenyl and naphthyl; carboxyl; hydrogen; cyano; or halo, for example, chloro, fluoro and the like; provided that in formula (II) at least two of $D^3$, $D^4$ and $D^5$ are saturated aliphatic of from 3 to 10 carbon atoms, e.g., propyl, butyl, heptyl and the like; Z is —O—, —N($D^6$)—, or —S—; and Y is

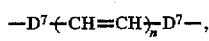

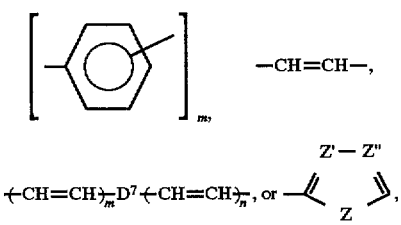

wherein:

m is an integer of from 0 to 4;

n is arylene of from 6 to 10 carbon atoms, for example, phenylene and naphthylene; and $D^6$ is hydrogen; a saturated aliphatic substituent of from 1 to 10 carbon atoms, such as an alkyl substituent; aryl of from 6 to 10 carbon atoms, such as phenyl or naphthyl; or a halo substituent, such as chloro or fluoro;

$D^7$ is arylene of from 6 to 10 carbon atoms, such as phenyl or naphthyl;

Z' and Z" are individually N or CH.

As used herein, "aliphatic" includes substituted aliphatic as well as unsubstituted aliphatic. The substituents in the case of substituted aliphatic include alkyl of from 1 to 5 carbon atoms, for example, methyl, ethyl, propyl and the like; aryl of from 6 to 10 carbon atoms, for example, phenyl and naphthyl; halo, such as chloro, fluoro and the like; nitro; and alkoxy having 1 to 5 carbon atoms, for example, methoxy, ethoxy, propoxy, and the like.

These above classes of host materials all produce blue-green fluorescence in a pure solid with a high quantum efficiency.

For white EL emission, portion of the electroluminescence is produced by the host material, and the other portion is necessarily produced by the red emitting guest material. Therefore, in construction the white EL emitting layer, it is important to select an appropriate range of concentrations of the guest molecule in the host matrix. Too high a concentration of guest molecule would produce an undesirable red hue from the guest, whereas too low a concentration would produce an equally undesirable blue-green hue from the host. It is found that the preferred range of concentration of the guest molecule in the blue green host is from 0.01 to 5.0% by mole ratio. Depending the efficiency of fluorescence energy transfer from the host to the guest molecule, choice of guest-host pair, it is understood that the concentration range can be substantially larger than indicated. The upper range of the guest molecule in the host matrix can as high as 10%.

The electron transport layer 116 of EL device 100 is a metal chelated oxinoid compound, including chelates of oxine itself (also commonly referred to as 8-quinolinol or 8-hydroxyquinoline). Such compounds exhibit both high levels of performance and are readily fabricated in the form of thin films. Exemplary of contemplated oxinoid compounds are those satisfying structural formula (XI).

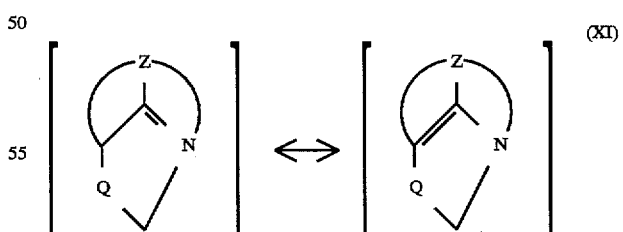

(XI)

wherein

Me represents a metal;

n is an integer of from 1 to 3; and

Z independently in each occurrence represents the atoms completing a nucleus having at least two fused aromatic rings.

From the foregoing it is apparent that the metal can be monovalent, divalent, or trivalent metal. The metal can, for example, be an alkali metal, such as lithium, sodium, or potassium; an alkaline earth metal, such as magnesium or calcium; or an earth metal, such as boron or aluminum. Generally any monovalent, divalent, or trivalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is preferably maintained at 18 or less.

Illustrative of useful chelated oxinoid compounds are the following:

Aluminum trisoxine [a.k.a, tris(8-quinolinol)aluminum, (Alq)]

Magnesium bisoxine [a.k.a. bis(8-quinolinol)-magnesium]

Indium trisoxine [a.k.a., tris(8-quinolinol)indium]

Lithum oxine (a.k.a., 8-quinolinol lithium)

In the organic EL devices of the invention, it is possible to maintain a current density compatible with efficient light emission while employing a relatively low voltage across the electrodes by limiting the total thickness of the organic luminescent medium to less than 10,000 Angstroms. At a thickness of less than 1 mm an applied voltage of 20 volts results in a field potential of greater than $2 \times 10^5$ volts/cm, which is compatible with efficient light emission. An order of magnitude reduction to 100 Angstroms in thickness of the organic luminescent medium, allowing further reductions in applied voltage and/or increase in the field potential and hence current density, are well within device construction capabilities.

The preferred materials for forming the organic luminescent medium are each capable of fabrication in the form of a thin film that is, capable of being fabricated as a continuous layer having a thickness of less than 5000 Angstroms. A preferred method for forming the organic luminescent medium is by vacuum vapor deposition. Extremely thin defect free continuous layers can be formed by this method. Specifically, individual layer thicknesses as low as about 50 Angstroms can be constructed while still realizing satisfactory EL device performance. Employing a vacuum vapor deposited porphorinic compound as a hole injecting layer, a film forming aromatic tertiary amine as a hole transporting layer (which can in turn be comprised of a triarylamine layer and a tetraaryldiamine layer), a fluorescent emitting layer comprised of a mixture of a host material and a fluorescent compound, and a chelated oxinoid compound as an electron injecting and transporting layer, individual layer thicknesses in the range of from about 50 to 5000 Angstroms are contemplated, with layer thicknesses in the range of from 100 to 2000 Angstroms being preferred. It is generally preferred that the overall thickness of the organic luminescent medium be at least about 1000 Angstroms.

The anode 104 and cathode 108 of the EL device 100 can each take any convenient conventional form. Where it is intended to transmit light from the EL device 100 through the anode, this can be conveniently achieved by coating a thin conductive layer onto a light transmissive substrate, e.g., a transparent or substantially transparent glass plate or plastic film. In one form the EL device 100 of this invention can follow the historical practice of including a light transmissive anode formed of tin oxide or indium tin oxide coated on a glass plate, as disclosed by Gurnee et al. U.S. Pat. No. 3,172,862, Gurnee U.S. Pat. No. 3,173,050, Dresner "Double Injection Electroluminescence in Anthracene", RCA Review, Volume 30, pages 322–334, 1969; and Dresner U.S. Pat. No. 3,710,167 cited above.

The EL device 100 of this invention can employ a cathode constructed of any metal, including any high or low work function metal, heretofore taught to be useful for this purpose. Unexpected fabrication, performance, and stability advantages have been realized by forming the cathode of a combination of a low work function metal and at least one other metal. For further disclosure, see commonly assigned U.S. Pat. No. 4,885,211 to Tang et al., the disclosure of which is incorporated by reference herein.

EXAMPLES

The following examples further illustrate the invention.

SYNTHESIS

Example 1

Preparation of 4,4-difluoro-1,3,5,7-tetraphenyl-4-bora-3a,4a,-diaza-indacene (G5)

To a mixture of 3,5-diphenyl-pyrrol-2-carboxaldehyde (0.9 g. 3.6 mmol), which was prepared from 2,4-diphenylpyrrole by Vilsmeier reaction, and 2,4-diphenylpyrrole (0.79 g, 3.6 mmol) in 120 mL of dry dichloromethane was added 0.4 mL of phosphorous oxychloride. The reaction mixture was stirred at room temperature overnight and was then added 2.4 mL of N,N-diisopropylethylamine, followed by addition of 2.4 mL of boron trifluoride etherate. After the reaction mixture was stirred at room temperature for three hours, it was washed with water. The organic layer was separated and then passed through the short silica gel column. After removal of solvents the dark purple 4,4-difluoro-1,3,5,7-tetraphenyl-4-bora-3a,4a,-diaza-s-indacene (1.56 g) was obtained in 87% yield. The pure material used for cell fabrication was obtained by sublimation at 285° C. under 2 Torr.

EL DEVICE FABRICATION AND PERFORMANCE

Example 2

Fabrication procedure

An EL device satisfying the requirements of the invention was constructed in the following manner. The device structure has a four organic-layer stack, namely hole-injecting layer, hole transporting layer, luminescent layer, electron-transporting layer.

a) An indium-tin-oxide coated glass substrate was sequentially ultrasonicated in a commercial detergent, rinsed in deionized water, degreased in toluene vapor and exposed to ultraviolet light and ozone for a few minutes.

b) A hole injecting layer of copper phthalocyanine (150 Angstroms) was then deposited on top of the ITO coated substrate by evaporation from a tantalum boat.

c) Onto the copper phthalocyanine layer was deposited a hole transporting layer of N,N'-BIS-(1-Naphthyl)-N, N'-Diphenylbenzidine, also evaporated from a tantalum boat.

d) A luminescent layer of host material (375 Angstroms) doped with a guest material was then deposited onto the hole transporting layer. This mixed layer was prepared by co-depositing the two materials from separate tantalum boats. The rates were independently controlled. The typical rate for host material was 5 Angstroms per second, and the rate for the guest material was adjusted according to the concentration desired.

e) A electron transporting layer of Alq (375 Angstroms) was then deposited onto the fluorescent emitting layer.

f) On top of the Alq layer was deposited a 2000 Angstroms cathode formed of a 10:1 atomic ratio of Mg and Ag.

The above sequence completed the deposition of the EL device. The device was then hermetically packaged in a dry glove box for protection against ambient environment.

Example 3

Preparation of white light emitting electroluminescent device

The EL devices were fabricated according to the procedure of Example 2. Except the fluorescent emitting layer was deposited with host material (H3) doped with various concentration of guest material, 4,4-difluoro-1,3,5,7-tetraphenyl-4-bora-3a,4a,-diaza-sindacene, (G5).

Table 1 lists the luminance quantum efficiency measured in unit of candela per square meter, CIE color coordinates, and the luminance output under a constant current bias of 20 mA/cm^2.

In the example, the best white emission is from a guest concentration of 0.05% with CIE color coordinates of X=0.356,=0.364, and a luminous sterance of 522 cd/m2 in a current density of 20 mA/cm2.

TABLE 1

| The CIE color coordinates and the luminance output under a constant current bias of 20 mA/cm^2. | | | | |
|---|---|---|---|---|
| Conc. of dopant | 0.0% | 0.05% | 0.1% | 0.25% |
| Cd/m^2 | 495 | 522 | 445 | 365 |
| Cie x | .2069 | .3555 | .4115 | .4640 |
| Cie y | .3352 | .3640 | .3656 | .3827 |

This result demonstrates the production of white light from single layer luminescent layer containing a red light emitting material uniformly dispersed in the host material in accordance with the present invention.

The invention has been described in detail with particular reference to certain preferred embodiments thereof, but it will be understood that variations and modifications can be effected within the spirit and scope of the invention.

| PARTS LIST |
|---|
| 100 electroluminescent device |
| 102 glass substrate |
| 104 anode |
| 106 organic electroluminescent medium |
| 108 cathode |
| 110 hole injection layer |
| 112 hole transport layer |
| 114 luminescent layer |
| 116 electron transport layer |
| 120 power source |
| 122 conductors |
| 124 conductors |
| 130 hole |
| 132 arrows |

-continued

| PARTS LIST |
|---|
| 140 electrons |
| 142 arrows |

We claim:

1. A white light emitting electroluminescent device, comprising:

a) an anode;

b) a hole transporting layer made of an organic compound;

c) a luminescent layer including a host material and a guest component uniformly dispersed in the host material;

d) a cathode;

e) said host material being selected to emit blue-green light; and f) the guest component being selected to emit red light and has the following formula and a concentration in the host material in the range of from 0.01 to 10% by mole ratio:

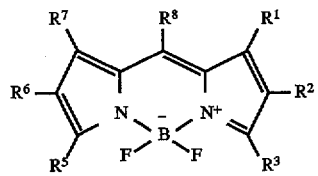

wherein $R^1$–$R^8$, which may be the same or different, are hydrogen, halogen, or alkyl, alkoxy, alkenyl, cycloalkyl, arylalkyl, acyl, wherein the alkyl portions each containing fewer than 24 carbons, or aryl heteroaryl, alone or in combination.

2. The white light emitting electroluminescent device of claim 1 wherein the host material comprises of a 8-quinolinol Aluminum complex of the formula:

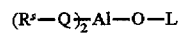

wherein Q in each occurrence represents a substituted 8-quinolinolato ligand, $R^S$ represents an 8-quionolinolato ring substituent chosen to block sterically the attachment of more than two substituted 8-quinolinolato ligands to the aluminum atoms, O—L is a phenolato ligand, and L is a hydrocarbon group that includes a aryl moiety.

3. The white light emitting electroluminescent device of claim 1 wherein the host material emits light in a range between 450–550 nm.

4. The white light emitting electroluminescent device of claim 2 wherein the host material has the following formula:

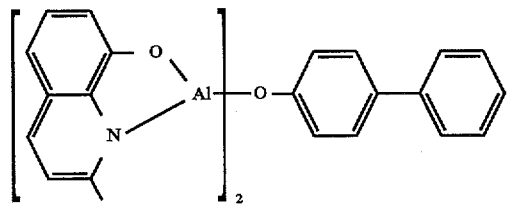

5. The white light emitting electroluminescent device of claim 2 wherein the guest material has the following formula:

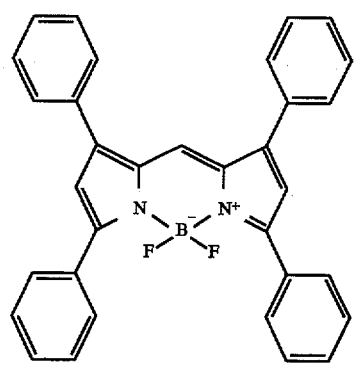
* * * * *